United States Patent [19]

Balzer

[11] Patent Number: 5,464,874
[45] Date of Patent: Nov. 7, 1995

[54] AQUEOUS SURFACTANT COMPOSITIONS OF ELEVATED VISCOSITY

[75] Inventor: Dieter Balzer, Haltern, Germany

[73] Assignee: Huels Aktiengesellschaft, Marl, Germany

[21] Appl. No.: 293,602

[22] Filed: Aug. 22, 1994

Related U.S. Application Data

[63] Continuation of Ser. No. 817,503, Jan. 7, 1992, abandoned.

[30]    Foreign Application Priority Data

Apr. 30, 1991 [DE] Germany .............. 41 14 141.5

[51] Int. Cl.[6] ............... A61K 7/48; A61K 7/50; C11D 3/48; C11D 9/50
[52] U.S. Cl. .............. 514/777; 252/106; 252/107; 424/70.1; 424/195.1; 424/70.11; 424/70.13; 514/782; 514/846; 514/847
[58] Field of Search .................... 514/777, 846

[56]    References Cited

U.S. PATENT DOCUMENTS

| | | | |
|---|---|---|---|
| 3,659,025 | 4/1972 | Halleck | 514/777 |
| 4,146,649 | 3/1979 | Siegel et al. | 514/847 |
| 4,159,318 | 6/1979 | Mausner et al. | 514/777 |
| 4,963,591 | 10/1990 | Fourman et al. | 424/68 |

FOREIGN PATENT DOCUMENTS

| | | |
|---|---|---|
| 0388810 | 9/1990 | European Pat. Off. . |
| 0384983 | 9/1990 | European Pat. Off. . |
| 0408965 | 1/1991 | European Pat. Off. . |
| WO91/14761 | 10/1991 | WIPO . |

*Primary Examiner*—Dale R. Ore
*Attorney, Agent, or Firm*—Oblon, Spivak, McClelland, Maier & Neustadt

[57]    ABSTRACT

A surfactant having an elevated viscosity is prepared with thickeners comprising an alkyl polyglycosides, polymer and optionally, a foreign electrolyte.

10 Claims, No Drawings

AQUEOUS SURFACTANT COMPOSITIONS OF ELEVATED VISCOSITY

This application is a Continuation of application Ser. No. 07/817,503, filed on Jan. 7, 1992, now abandoned.

BACKGROUND OF THE INVENTION

1. Field of the Invention

The present invention relates to aqueous surfactant compositions having elevated viscosity which have a low foreign electrolyte content. In particular, the present invention relating to aqueous surfactant compositions may be used in cosmetic compositions such as, for example, shampoos, bath and shower preparations, hand-wash pastes and lotions.

2. Background Information

High viscosity aqueous surfactants are desirable in many cases. They are easier to handle and can be metered simply. If the composition contains a second phase (solid or liquid), the elevated viscosity also imparts higher storage stability. Moreover, higher viscosity aqueous surfactant compositions are of interest for marketing reasons, since the consumer frequently associates preparations of low viscosity with a low concentration of the active compound.

Aqueous surfactant compositions usually contain anionic surfactants, such as, fatty alcohol ether-sulphates, fatty alcohol sulphates, fatty alcohol sulphosuccinates, alkane sulphonates or ethercarboxylic acids, as the main component, and are sometimes found in combination with betaines, ampholytic compounds or fatty acid alkanolamides, for example. In the case of fatty alcohol ether sulphates and fatty alcohol sulphates, a simple increase in the viscosity can be obtained by adding water-soluble inorganic salts (foreign electrolytes), such as NaCl, $NH_4Cl$ and $Na_2SO_4$, but the amount of electrolytes which needs to be added are fairly high, which is undesirable, since in higher concentrations the electrolytes may be irritating. Many other surfactants which are of particular interest for use in the above compositions because of their high tolerance by the skin or mucous membranes, either cannot be thickened or can be thickened only to a small extent by adding foreign electrolytes.

Fatty acid alkanolamides can be used as a consistency regulator, but are considered undesirable since the low content of free alkanolamine can give rise to the formation of nitrosamine as a byproduct. Nitrogen-free additives are therefore preferred, instead of the alkanolamides (compare H. Hensen et al., 2nd World Surfactant Congress, Paris 1988, Vol. II, pages 378 ff.).

Saturated or unsaturated fatty alcohol oxethylates having low degrees of ethoxylation, preferably containing about 2.5 mol EO/mol (A. Behler et al., Seifen, Öle, Fette, Wachse 116, 60 (1990)) constitute one solution to this problem, but are also considered to be somewhat disadvantageous since they possess very high fat-dissolving power and their limited solubility in water reduces their foamability. Moreover, their effectiveness in compositions simulating those used in practice, that is to say, with realistic amount of the electrolyte is restricted to sulphate surfactants (A. Behler et al. loc. cit.).

Thickeners for aqueous solutions, which are effective irrespective of the surfactant type, belong to the group of water-soluble polymers. Suitable additives here are cellulose derivatives and xanthans. Polyethylene glycol derivatives (German Patent 3,140,160), polyol monoethers (European Patent 0,303,187), fatty acid-esterified polyoxyalkylene ethers of glycerol or propane-1,2-diol (German Patent 3,239,564) or other polyhydric alcohols (German Patent 3,843,224), and alkylpolyethylene glycol ether fatty acid esters (German Patent 3,541,813), for example, have also been disclosed. The thickening action of these additives is presumably due to a highly hydrated lattice build up, resulting in the partial immobilization of water. In this case, a certain synergism is also sometimes observed between the surfactant and the polymer, but the polymer concentration required to obtain the desired viscosity value is so high that the final aqueous solution is relatively expensive. Also the use of polymers such as those based on polyethylene glycol is questionable from an ecological point of view since said polymers, are not adequately biodegradable.

In addition, there are processing disadvantages and sometimes unsatisfactory rheological characteristics that arise in the case of high polymer concentrations. Therefore, polymers should only be used in very low concentrations in cosmetic compositions.

A thickener mixture is described in German Patent 3,843,224 which utilizes the surfactant/polymer combination in a targeted manner for surfactant compositions. The patent claims a mixture of a nonionic surfactant (HLB value of 4 to 11) with a polymer in a weight ratio of 10:1 to 1:10 as a thickener for other surfactant mixtures. Typical nonionic surfactants disclosed are oxethylates having low degrees of EO, that is to say, precisely those surfactants which, although they have a considerable thickening effect are questionable both toxicologically in respect to their tolerance by the skin and mucous membranes, and ecologically (compare P. Schöbel et al., Tenside Surfactants Detergents 25.2 (1988), S. Matsumura JAOCS 67, p. 996 (1990)).

Thus, the need exists for a thickener mixture that would increase the viscosity of an aqueous, cosmetic surfactant composition without the disadvantages described above. The present invention provides for such a composition that is toxicologically, ecologically and economically superior to any previously known surfactant composition.

The present invention has achieved this objective by providing an aqueous surfactant composition that comprises a mixture of surfactant, polymer, and optionally an electrolyte, as a thickener to a surfactant base composition.

SUMMARY OF THE INVENTION

The present invention provides for an aqueous, cosmetic surfactant composition with an elevated viscosity comprising 4 to 30% by weight of base surfactants, and 3 to 29.5% by weight of a thickener mixture and additive, wherein the thickener mixture comprises 3 to 25% by weight of an alkyl polyglycoside, 0.005 to 2% by weight of a polymer and 0 to 2.5% by weight of a foreign electrolyte wherein the weight percentages are based on the aqueous, cosmetic surfactant composition.

In another embodiment, the present invention relates to the aqueous cosmetic surfactant composition described above further characterized in that the alkyl polyglycoside has the formula I of $R-O-Z_n$ in which R represents an alkyl radical having 8 to 18 C atoms, or a mixture thereof, and $Z_n$ represents a polyglycoside radical where n=1 to 5 hexose or pentose units, or a mixture thereof.

In yet another embodiment, the present invention relates to the aqueous cosmetic surfactant composition described above wherein the alkyl polyglycoside is an alkyl polyglycoside having a HLB value of between 11.5 and 17.

In another embodiment, the present invention relates to the aqueous cosmetic surfactant composition described above that is further characterized in that the above polymer is a fatty alcohol ether or fatty acid ester having $C_8$–$C_{20}$ chains or a mixture of alkoxylated polyhydric alcohols. The alkoxylate may be an ethoxylate and the degree of ethoxylation is between 20 and 500. The polyhydric alcohols may further comprise between 2 to 8 carbon atoms.

In yet a further embodiment, the present invention relates to the aqueous cosmetic surfactant composition described above wherein the polymer is a $C_8$–$C_{20}$-fatty acid ester of alkoxylated $C_8$–$C_{20}$-fatty alcohols.

In another embodiment, the polymer of the aqueous cosmetic surfactant composition described above is a fatty acid diester or fatty alcohol diether of a polyglycol ether having an average molar weight of between 2,000 and 25,000.

Various other objects and advantages of the present invention will become apparent from the following description of the invention.

DETAILED DESCRIPTION OF THE INVENTION

The present invention relates to aqueous cosmetic surfactant compositions of elevated viscosity containing 4 to 30% by weight of base surfactants, and 3 to 29.5% by weight of a thickener mixture and additive. The compositions are characterized in that the thickener mixture contains 3 to 25% by weight of alkyl polyglycoside, 0.005 to 2% by weight of a polymer and 0 to 2.5% by weight of a foreign electrolyte based on the aqueous, cosmetic surfactant composition.

It has been found, surprisingly, that sufficiently high viscosities are achieved in cosmetic surfactant compositions by means of the alkyl polyglycosides used according to the present invention in combination with extremely small amounts of polymer and, optionally by addition of a small amount of a foreign electrolyte.

For a base surfactant content in the composition of 4 to 30% preferably 5 to 25%, the recommended thickener mixture is as follows: 3 to 25% by weight of an alkyl polyglycoside, 0.005 to 2% by weight of a polymer, preferably 0.01 to 1.5%, and 0 to 2.5%, preferably 0 to 2% by weight, of a foreign electrolyte.

Base surfactants are surfactants customary in aqueous cosmetic compositions, such as, in particular, fatty alcohol ether-sulphates, fatty alcohol sulphates, carboxymethylated fatty alcohol oxethylates, sulphosuccinates, alkane sulphonates, fatty acid salts, betaines, ampholytic compounds, fatty alcohol oxethylates, sorbitane esters, ethoxylated sorbitane esters, sugar esters or a mixture thereof.

The alkyl polyglycosides according to the present invention satisfy the formula I:

$$R—O—Z_n \qquad (I)$$

wherein R represents an alkyl radical having 8 to 18, preferably 10 to 18 carbon atoms, or a mixture thereof, and $Z_n$ represents a polyglycosyl radical where n =1 to 5, preferably 1.1 to 3 hexose or pentose units, or a mixture thereof. The alkyl radical may be straight-chained or branched, and either saturated or unsaturated.

Alkyl polyglycosides containing fatty alkyl radicals having between 12 to 16 carbon atoms and a polyglycosyl radical in which n =1.1 to 2.5 are preferred. Alkyl polyglycosides having an HLB value between 11.5 and 17, which can be determined, for example, via the emulsion method are particularly preferred.

The alkyl polyglycosides used according to the present invention can be prepared by known processes on the basis of raw materials which undergo secondary expansion. For example, dextrose is reacted in the presence of an acid catalyst with n-butanol to form butyl polyglycoside mixtures. These mixtures are subjected to transglycosidation with long-chain alcohols in the presence of an acid catalyst to give the desired alkyl polyglycoside mixtures.

The structure of the product can be varied within certain limits. The alkyl radical R is determined by the choice of the long-chain alcohol. The most economical surfactant alcohols have between 10 to 18 C atoms, in particular, those having naturally occurring fatty alcohols from the hydrogenation of fatty acids or fatty acid derivatives are preferred, which are also available industrially. Ziegler alcohol or oxo alcohols may also be used.

The polyglycosyl radical $Z_n$ is determined either by the choice of the carbohydrate or by the adjustment of the average degree of polymerization n, for example, in accordance with German Offenlegungsschrift (German Published Specification) 1,943,689. In principle, as is known, polysaccharides, for example, starch, maltodextrines, dextrose, galactose, mannose, or xylose, for example, may be used. The industrially available carbohydrates, starch, maltodextrines and especially dextrose are preferred. Since the alkyl polyglycoside syntheses which are economically worthwhile do not proceed regio- and stereoselectively, the alkyl polyglycosides are always mixtures of oligomers, which in turn, are mixtures of various isomeric forms. They are present alongside one another with α- and β-glycoside bonds in pyranose and furanose form. The points of linkage between the two saccharide radicals also differ.

Alkyl polyglycosides used according to the present invention may also be prepared by admixing alkyl polyglycosides with alkyl monoglycosides. The latter can be isolated or concentrated from alkyl polyglycosides, for example, in accordance with EP-A-0,092,355 using polar solvents, such as acetone.

The degree of glycosidation is appropriately determined by means of $^1$H-NMR.

The alkyl polyglycosides are regarded as extremely environmentally friendly when compared with all other surfactants used in cosmetic cleansing agents. The degree of biological degradation of the alkyl polyglycosides according to the present invention is very high, measuring 96±3% when analyzed with a water treatment plant simulation 1l/DOC model. This figure is measured against a background that regards as readily degradable a substance that has a 70% degree of degradation.

The acute oral toxicity LD 50 (rat) and the aquatic toxicity (LC 50 (golden orfe) and EC 50 (Daphnia), at values of >10,000 mg/kg, 12 mg/l and 30 mg/l respectively, are more favorable by a factor of 3 to 5 than the corresponding values of the current most important surfactants. The same is true of the skin and mucosa tolerance which is particularly important in the case of cosmetic compositions.

Polymers according to the present invention are, in particular, derivatives of alkoxylated, and in particular, ethoxylated, polyhydric alcohols having 2 to 8 C atoms, such as ethylene glycol, propanediol, glycerol, butandiol, erythritol, pentaerythritol, arabitol, or sorbitol, for example. Preferred derivatives are fatty acid esters and fatty alcohol ethers, the saturated or unsaturated, straight-chain or branched alkyl radicals being able to possess 8 to 20 carbon atoms and the average degree of alkoxylation being 20 to 500 mol/mol.

Further preferred polymers and fatty acid esters of alkoxylated, in particular, ethoxylated, fatty alcohols have the formula II $$R'-O(C_2H_4O)_m COOR'' \qquad (II)$$

in which R' is a straight-chain (or optionally branched), saturated or unsaturated, alkyl radical having 8 to 20 carbon atoms, or a mixture thereof, R" is a straight-chain (or optionally branched) saturated or unsaturated, alkyl radical having 8 to 20 carbon atoms, or a mixture thereof, and m is an average number from 20 to 100.

The fatty acid esters and/or fatty alcohol ethers of the polyglycol ethers having average molar masses between 2,000 and 25,000 are the preferred polymers. The alcohol end groups of the polyglycol ethers must substantially completely esterified or etherified.

Polymers based on cellulose or xanthan are also suitable polymers but they are less preferred. Polymer mixtures can also be used.

The surfactants customarily regarded as base surfactants in aqueous cosmetic compositions of the present invention are, in particular, fatty alcohol ether-sulphates, fatty alcohol sulphates, carboxymethylated fatty alcohol oxethylates, fatty alcohol ether-sulphosuccinates, alkane sulphonates, fatty acid salts, alkyl betaines, ampholytic compounds, fatty alcohol oxethylates, fatty acid sorbitane esters, ethoxylated sorbitane esters, sugar esters, and a mixture thereof, the chain length of the saturated or unsaturated, straight-chain or branched alkyl chain being in each case 8 to 22, preferably 10 to 20, carbon atoms, and the cations of the anionic surfactants are Na, K, $NH_4$, $C_2$-$C_3$-alkanolammonium or Mg. The degrees of ethoxylation are between 1 and 5 (preferably between 2 and 4) mol of ethylene oxide/mol in the case of the fatty alcohol ether-sulphates, between 2 and 15 (3 to 10) ml of ethylene oxide/mol in the case of the carboxylated oxethylates, between 1 and 6 (2 to 4) mol of ethylene oxide/mol in the case of the fatty alcohol ether-sulphosuccinates and between 2 and 25 (2–15) mol of ethylene oxide/mol in the case of the fatty alcohol oxethylates.

The viscosity of the aqueous surfactant compositions for cosmetic compositions according to the present invention may, if appropriate, be optimized by the addition of water-soluble electrolytes. Thus, the addition of these substances is advisable. Electrolytes which may be used for this purpose are, inter alia, alkali metal halides, sulphates or phosphates, ammonium halides, sulphate or phosphates, and alkaline earth metal halides, sulphates or phosphates.

The aqueous compositions according to the present invention may contain further components which are of importance for the particular application. Suitable components are, for example, silicone surfactants, hydrolyzed proteins, scents, turbidity and opalescent agents, fat restorers, silicone oils, humectants, preservatives, skin-cosmetic active compounds, plant extracts, buffers and complexing agents.

The following examples are intended to further illustrate the present invention without being deemed limitative thereof.

EXAMPLES

Example 1

5 g of carboxymethylated $C_{12}$–$C_{14}$-fatty alcohol oxethylate containing 4 mol of EO/mol (degree of carboxymethylation 95%), 5 g of $C_{12}$–$C_{14}$-alkyl polyglycoside (degree of glycosidation 1.3, HLB value 13.0) and 0.4 g of Antil® 141 solid were dissolved in water at 50–60° C. 1 g of NaCl was added and the solution was made up to 100 ml with water. The viscosity of the solution at shear rates of about 10 $sec^{-1}$ was 3,500 mPa.s. Antil® 141 is PEG-55 propylene glycol dioleate.

Example 2 (Comparison Example)

10 g of carboxymethylated $C_{12}$–$C_{14}$-fatty alcohol oxethylate (degree of carboxymethylation 95%) and 0.4 g of Antil® 141 solid were dissolved in water, and NaCl was added to the solution, as in Example 1. The viscosity, measured as in Example 1, was 2 mPa.s and compared with that of the pure surfactant solution, to which 1% NaCl was added, was not increased by the polymer.

The comparison of Examples 1 and 2 shows the exceptionally synergistic thickening action of the alkyl polyglycoside and polymer mixture even at low electrolyte concentrations in the case of an anionic surfactant which otherwise can be thickened only with difficulty.

Example 3

Sorbitol was ethoxylated (about 300 mol of EO/mol) at about 170° C. in the presence of NaOH and then esterified with stearic acid at about 210° C. and 30 mbar in the presence of isopropyl titanate as catalyst. The reaction is complete after about 8 h and the establishment of a OH number of ≦5 mg KOH/g. The product, sorbital 300 EO hexastearate, has a softening point of about 60°C.

The polymer prepared in this way is added in various concentrations to aqueous solutions of various mixtures of $C_{12}$–$C_{14}$-fatty alcohol ether-sulphate containing 2 mol of EO/mol and $C_{12}$–$C_{14}$-alkyl polyglycoside (degree of glycosidation 1.5, HLB value 13,8) in the presence of 1% NaCl.

Whereas pure fatty alcohol ether-sulphate can virtually not be thickened by the added polymer in the concentration range under consideration, the increase in viscosity in the presence of the alkyl polyglycoside is extremely high. With 15% detergent substance and an FAES/APG ratio of 1:1, 0.03% of the polymer already suffices to achieve a viscosity of about 5,000 mPa.s, which is typical for a shampoo. The compositions according to the present invention display outstanding foaming power (Wilmsmann friction foam, 2 g/l) in the presence or absence of artificial sebum (30% triolein, 20% tristearin, 20% squalane, 15% oleic acid, 10% palmitic acid, 5% stearic acid) in comparison with commercially available shampoos.

Example 4

0.4 g of the sorbitol polymer from Example 3 was added to 7.5 g of $C_{12}$–$C_{14}$-fatty alcohol ether-sulphate containing 2 mol of (EO/mol and 7.5 g of $C_{12}$–$C_{14}$-alkyl polyglycoside having a degree of glycosidation of 1.5 (HLB value 13.8) and the solution was made up to 100 ml with water. The viscosity of the clear solution, measured at a shear rate of about 10 $sec^{-1}$, was about 5,000 mPa.s.

The example demonstrates that in the case of the composition according to the present invention, thickening appropriate for a shampoo can be achieved even with very low polymer concentrations without a foreign electrolyte.

Example 5

526 g of LIPOXOL® 4,000 (polyethylene glycol, average molar mass 4,000), 73.7 g of oleic acid and 0.6 g of isopropyl titanate were heated at 180° C. under a water pump vacuum for about 20 h until an acid number of <1 mg KOH/g was obtained.

1 g of the diester prepared in this way was added to 100 ml of aqueous solution containing 7.5% of carboxymethylated $C_{12}$–$C_{14}$-fatty alcohol oxethylate containing 4 mol of EO/mol, 7.5% Of $C_{12}$–$C_{14}$-alkyl polyglycoside (degree of glycosidation 1.5) and 1% of NaCl. The viscosity of this solution was about 5,200 mPa.s; the foaming power in the presence or absence of sebum is very good and is higher than that of various products on the market.

Example 6

0.3% of the sorbitol polymer from Example 3 was added to an aqueous solution containing 7.5% of coconut-amidopropyl betaine and 7.5% of $C_{12}$–$C_{14}$-alkyl polyglycoside (degree of glycosidation 1.3); the betaine contained 2.2% of NaCl originating from its preparation. The viscosity of the clear solution was 6,000 mPa.s. In contrast, the viscosity of a 15% strength betaine solution of the same polymer concentration and electrolyte content was 4 mPa.s. The comparison of the values demonstrates the outstanding consistency-regulating effect of the formulation according to the invention.

Example 7

1% of Antil® solid was added to an aqueous solution containing 5% of $C_{12}$–$C_{14}$-fatty alcohol ethoxylate-sulphosuccinate and about 3 mol of EO/mol, 5% of $C_{12}$–$C_{14}$-alkyl polyglycoside (degree of glycosidation 1.3) and 1% of NaCl. The viscosity of the resulting clear gel is 17,000 mPa.s, measured at a shear rate of about 10 sec$^{-1}$.

Example 8

0.8% of sorbitol polymer (compare Example 3) is added to an aqueous solution containing 5% of $C_{12}$–$C_{14}$-fatty alcohol ether-sulphate (2 mol of EO/mol), 5% of $C_{10}$–$C_{12}$-alkyl polyglycoside (HLB value 14.5) and 1% of NaCl. The viscosity of the solution is about 4,500 mPa.s, the clear point is 2° C. and the foaming power is outstanding.

Example 9

1% of Antil® 141 solid of added to an aqueous solution containing 5% of $C_{12}$–$C_{14}$-fatty alcohol ether-sulphate (e mol of EO/mol), 5% of $C_{12}$–$C_{14}$-alkyl polyglycoside (degree of glycosidation 1.5) and 1% of NaCl. The resulting gel has a viscosity of about 15,000 mPa.s at a shear rate of 10 sec$^{-1}$ and a clear point of 5° C.

All publications mentioned hereinabove are hereby incorporated by reference.

While the foregoing invention has been described in some detail for purposes of clarity and understanding, it will be appreciated by one skilled in the art from reading of this disclosure that various changes in form and detail can be made without departing from the true scope of the invention.

What is claimed is:

1. In an aqueous cosmetic surfactant composition of elevated viscosity comprising 4 to 30% by weight of a base surfactant and 3 to 29.5% by weight of a thickener mixture and additive, the improvement wherein the thickener mixture and additive comprises (A) 3 to 25% by weight of an alkyl polyglycoside having the formula R—O—$Z_n$, in which R is an alkyl radical having 8 to 18 carbon atoms, or a mixture thereof, and $Z_n$ represents a polyglycoside where n=1 to 5 and Z represents a hexose or pentose unit, or a mixture thereof, (B) 0.005 to 2% by weight of a polymer selected from the group consisting of
  (1) fatty acid esters of alkoxylated polyhydric alcohols having 3 to 8 carbon atoms and 3 to 6 hydroxyl groups, wherein the average degree of alkoxylation is 20–500 mol/mol;
  (2) fatty alcohol ethers of alkoxylated polyhydric alcohols having 3 to 8 carbon atoms and 3 to 6 hydroxyl groups wherein the average degree of alkoxylation is 20–500 mol/mol;
  (3) fatty acid esters of alkoxylated fatty alcohols;
  (4) fatty acid diesters of polyglycol ethers having average molecular weights between 2,000 and 25,000;
  (5) fatty alcohol diethers of polyglycol ethers having average molecular weights between 2,000 and 25,000;
  (6) xanthan polymers; and
  (7) compounds of the formula R'—O($C_2H_4O$)$_m$COOR", in which R' and R" are independently selected alkyl groups having 8 to 20 carbon atoms, and m is an average number from 20 to 100; and (C) 0 to 2.5% by weight of a foreign electrolyte selected from the group consisting of alkali metal halides, alkali metal sulfates, ammonium phosphates, alkaline earth metal halides, alkaline earth metal sulfates, and alkali metal phosphates, wherein said weight percentages are based on the aqueous cosmetic surfactant composition.

2. An aqueous cosmetic surfactant composition according to claim 1 wherein (B) is sorbitol 300 EO hexastearate.

3. The aqueous, cosmetic surfactant composition of claim 1, wherein the alkyl polyglycoside is an alkyl polyglycoside having a HLB value of between 11.5 and 17.

4. The aqueous cosmetic surfactant composition according to claim 1, wherein the polymer is a fatty alcohol ether or fatty acid ester having $C_8$–$C_{20}$ chains or a mixture of alkoxylated polyhydric alcohols having 2 to 8 carbon atoms.

5. The aqueous cosmetic surfactant composition according to claim 1, wherein the alkoxylate is an ethoxylate, and the degree of ethoxylation is between 20 and 500.

6. The aqueous cosmetic surfactant composition of claim 1, wherein the polyhydric alcohols comprises 2 to 8 carbon atoms.

7. The aqueous cosmetic surfactant composition according to claim 1, wherein the polymer is a $C_8$–$C_{20}$-fatty acid ester of alkoxylated $C_8$–$C_{20}$-fatty alcohols.

8. The aqueous cosmetic surfactant composition according to claim 1, wherein the polymer is a fatty acid diester or fatty alcohol diether derivative of a polyglycol ether having an average molecular weight of between 2,000 and 25,000.

9. An aqueous cosmetic surfactant composition according to claim 1 wherein (B) is polyglycol dioleate in which the polyglycol has an average molecular weight between 2,000 and 25,000.

10. An aqueous cosmetic surfactant composition according to claim 1 wherein (B) is polyethylene glycol dioleate in which the polyethylene glycol has an average molecular weight of 4,000.

* * * * *